(12) United States Patent
Yu et al.

(10) Patent No.: US 12,238,837 B2
(45) Date of Patent: Feb. 25, 2025

(54) CIRCUIT CONFIGURATION METHOD FOR IMPROVING EFFICACY OF ANTIBACTERIAL LAMP, VOLTAGE BOOST CIRCUIT, AND ANTIBACTERIAL LAMP

(71) Applicant: sintexx technology co., LTD., Taoyuan (TW)

(72) Inventors: Yi-Chang Yu, Taoyuan (TW); Toshiyuki Sugiyama, Taoyuan (TW)

(73) Assignee: SINTEXX TECHNOLOGY CO., LTD., Taoyuan (TW)

( * ) Notice: Subject to any disclaimer, the term of this patent is extended or adjusted under 35 U.S.C. 154(b) by 232 days.

(21) Appl. No.: 18/184,646

(22) Filed: Mar. 15, 2023

(65) Prior Publication Data

US 2023/0300960 A1 Sep. 21, 2023

(30) Foreign Application Priority Data

Mar. 16, 2022 (TW) .................................. 111109525
Apr. 1, 2022 (TW) .................................. 111112726

(51) Int. Cl.
| | |
|---|---|
| *H05B 45/38* | (2020.01) |
| *A61L 2/03* | (2006.01) |
| *A61L 2/238* | (2006.01) |
| *A61L 2/26* | (2006.01) |
| *F21S 4/10* | (2016.01) |
| *F21V 23/00* | (2015.01) |
| *F21V 23/06* | (2006.01) |

(52) U.S. Cl.
CPC .............. *H05B 45/38* (2020.01); *A61L 2/035* (2013.01); *A61L 2/238* (2013.01); *A61L 2/26* (2013.01); *A61L 2202/11* (2013.01)

(58) Field of Classification Search
CPC .......... H05B 45/38; F21S 4/10; F21V 23/007; F21V 23/06; A61L 2/035; A61L 2/238; A61L 2/26
See application file for complete search history.

(56) References Cited

U.S. PATENT DOCUMENTS

| | | | |
|---|---|---|---|
| 2013/0285550 A1* | 10/2013 | Chang | H02M 7/06 315/85 |
| 2024/0302006 A1* | 9/2024 | Chow | F21V 23/06 |

FOREIGN PATENT DOCUMENTS

| | | |
|---|---|---|
| CN | 103957641 A | 7/2014 |
| TW | 201101926 A1 | 1/2011 |

* cited by examiner

*Primary Examiner* — Joseph L Williams
(74) *Attorney, Agent, or Firm* — Birch, Stewart, Kolasch & Birch, LLP

(57) ABSTRACT

A circuit configuration method for improving efficacy of antibacterial lamps, a voltage boost circuit, and an antibacterial lamp are provided. The voltage boost circuit includes a primary side, a first secondary side, and a second secondary side. An electromagnetic induction occurs between the first secondary side and the primary side to generate a first high voltage, and the first secondary side includes a first connecting terminal and a first grounding terminal. The second secondary side is electrically coupled to the first ground terminal, and an electromagnetic induction occurs between the second secondary side and the primary side to generate a second high voltage that is not equal to the first high voltage. The second secondary side includes a second connecting terminal, and the second connecting terminal and the first connecting terminal are configured to be used to connect with a load.

14 Claims, 20 Drawing Sheets

CIRCUIT CONFIGURATION METHOD FOR IMPROVING EFFICACY OF ANTIBACTERIAL LAMP, VOLTAGE BOOST CIRCUIT, AND ANTIBACTERIAL LAMP

CROSS-REFERENCE TO RELATED PATENT APPLICATION

This application claims the benefit of priorities to Taiwan Patent Application No. 111109525, filed on Mar. 16, 2022, and Ser. No. 11/112,726, filed on Apr. 1, 2022. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a method, a circuit, and a lamp, and more particularly to a circuit configuration method for improving efficacy of antibacterial lamp, a voltage boost circuit, and an antibacterial lamp.

BACKGROUND OF THE DISCLOSURE

A common light emitting device that is available on the market uses light emitting diodes as a light source. The light emitting device is arranged in such a way that a plurality of light emitting diodes are connected in series to form a string of light emitting diodes, and a positive terminal and a negative terminal of the string of light emitting diodes are connected to a power supply circuit to achieve a purpose of lighting.

However, when the light emitting device is connected to a conventional power supply circuit, a voltage received (or used) by each of the light emitting diodes will depend on a quantity of light emitting diodes connected in series, and the voltage is usually within a range from 3 volts to 300 volts (where the quantity of the light emitting diodes connected in series is 100), so that a working voltage of the light emitting device is not high. Hence, when the light emitting device requires a high voltage electric field (e.g., using the high-voltage electric field to excite nano-silver to produce silver ions), the design of the conventional power supply circuit can indirectly cause the light emitting diodes to be unable to achieve the effect of high voltage electric field. Therefore, one of the issues to be addressed in the relevant industry is how to provide light emitting diodes that operate on low voltage with characteristics of high-voltage operation.

SUMMARY OF THE DISCLOSURE

In response to the above-referenced technical inadequacies, the present disclosure provides a circuit configuration method for improving efficacy of antibacterial lamp, a voltage boost circuit, and an antibacterial lamp.

In order to solve the above-mentioned problems, one of the technical aspects adopted by the present disclosure is to provide a circuit configuration method for improving the efficacy of an antibacterial lamp. The circuit configuration method includes: providing an alternating voltage to a rectifier circuit and a boost loop; using the rectifier circuit to rectify the alternating voltage into a direct voltage and providing a first voltage level; using the boost loop to increase the direct voltage to a second voltage level; and combining the first voltage level and the second voltage level into a high voltage level to provide for a driving circuit to drive the antibacterial lamp.

In order to solve the above-mentioned problems, another of the technical aspects adopted by the present disclosure is to provide an antibacterial lamp derived by the circuit configuration method, and the antibacterial lamp includes a translucent cover, a substrate, a plurality of light emitting diode chips, and a nanometer coating. The translucent cover has an accommodating space. The substrate is disposed in the accommodating space. The light emitting diode chips are disposed on the substrate. The light emitting diode chips are connected in series to form a high-voltage circuit. When the high-voltage circuit is powered, the high-voltage circuit is configured to generate a high-voltage electric field surrounding the translucent cover. The nanometer coating is disposed on the translucent cover. The nanometer coating is configured to be irradiated by the high-voltage electric field to dissociate antibacterial ions.

In order to solve the above-mentioned problems, yet another of the technical aspects adopted by the present disclosure is to provide a voltage boost circuit for providing an antibacterial lamp. The voltage boost circuit includes a primary side, a first secondary side, and a second secondary side. The first secondary side includes a first connecting terminal and a first grounding terminal. A first high voltage is generated between the first secondary side and the primary side by electromagnetic induction. The second secondary side is electrically coupled to the first ground terminal. A second high voltage is generated between the second secondary side and the primary side by electromagnetic induction that is not equal to the first high voltage. The second secondary side includes a second connecting terminal, and the second connecting terminal and the first connecting terminal are configured to be used to connect with a load.

In order to solve the above-mentioned problems, still another of the technical aspects adopted by the present disclosure is to provide a voltage boost circuit for an antibacterial lamp. The voltage boost circuit includes a rectifier module, two boost loops, and an integrated circuit control module. The rectifier module is configured to electrically couple an AC power source to output a DC power source. One of the two boost loops is configured to boost the AC power source to provide a first voltage level, and another one of the two boost loops is configured to boost the DC power source to provide a second voltage level. The integrated circuit control module controls to the second voltage level combined with the first voltage level to form a high voltage level, so as to drive the antibacterial lamp.

Therefore, the circuit configuration method, the voltage boost circuit, and the antibacterial lamp provided by the present disclosure, by virtue of "the first voltage level and the second voltage level being combined into a high voltage level," the circuit configuration method, the voltage boost circuit, and the antibacterial lamp can provide a high voltage with a small load voltage difference to improve the antibacterial effect of the antibacterial lamp.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
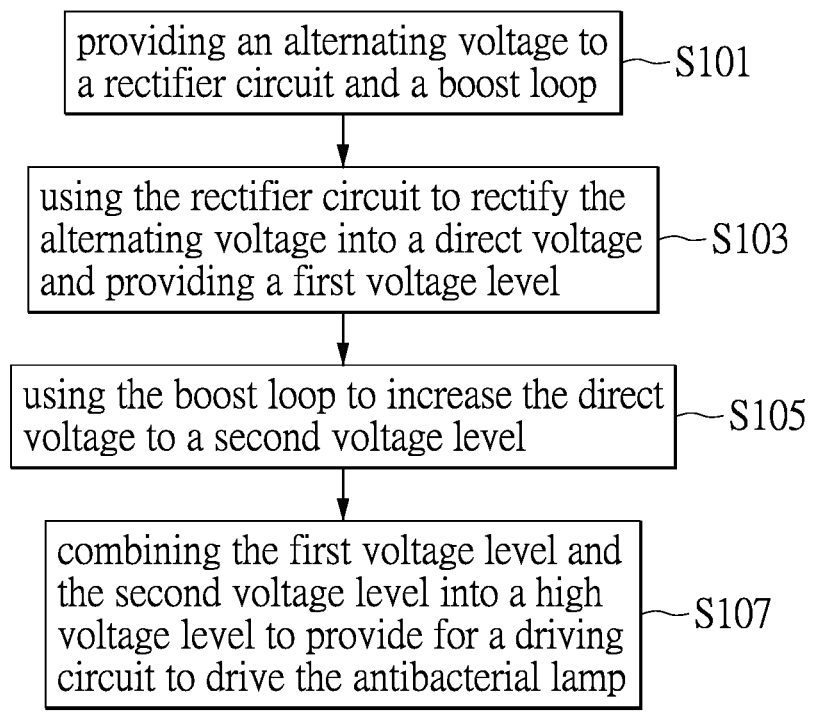
FIG. 1 is a flowchart of a circuit configuration method according to a first embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a," "an" and "the" includes plural reference, and the meaning of "in" includes "in" and "on." Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first," "second" or "third" can be used to describe various components, signals or the like, which are for distinguishing one component/signal from another one only, and are not intended to, nor should be construed to impose any substantive limitations on the components, signals or the like.

First Embodiment

Figure 2:
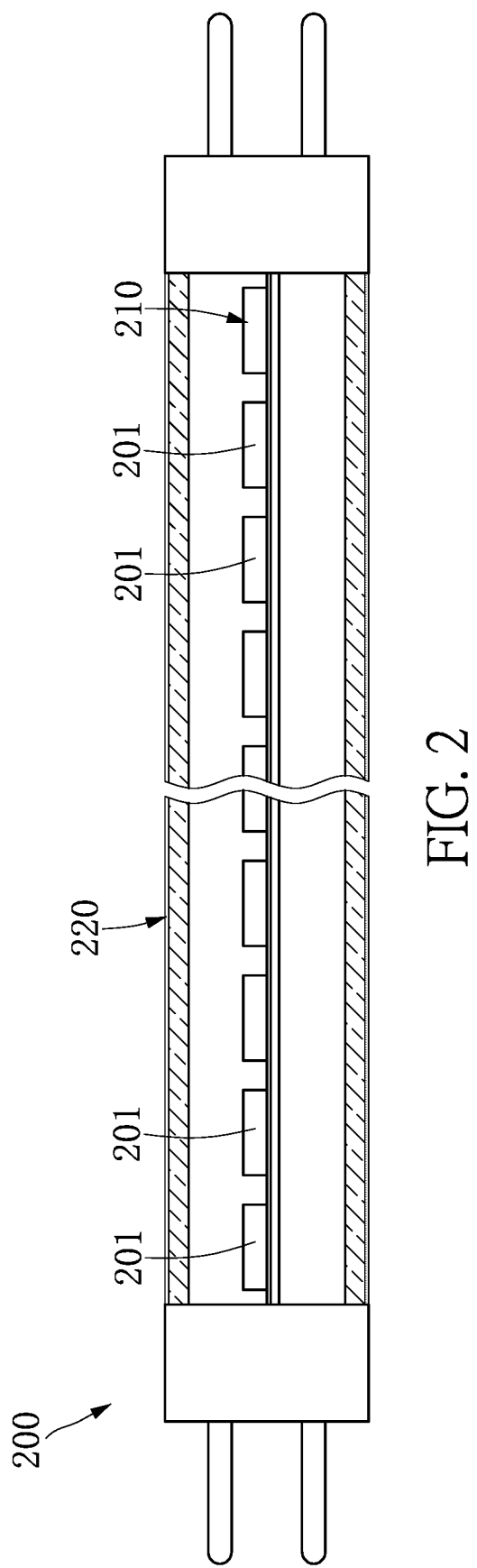
FIG. 2 is a schematic view of an antibacterial lamp applying the circuit configuration method according to the first embodiment of the present disclosure.
Figure 3:
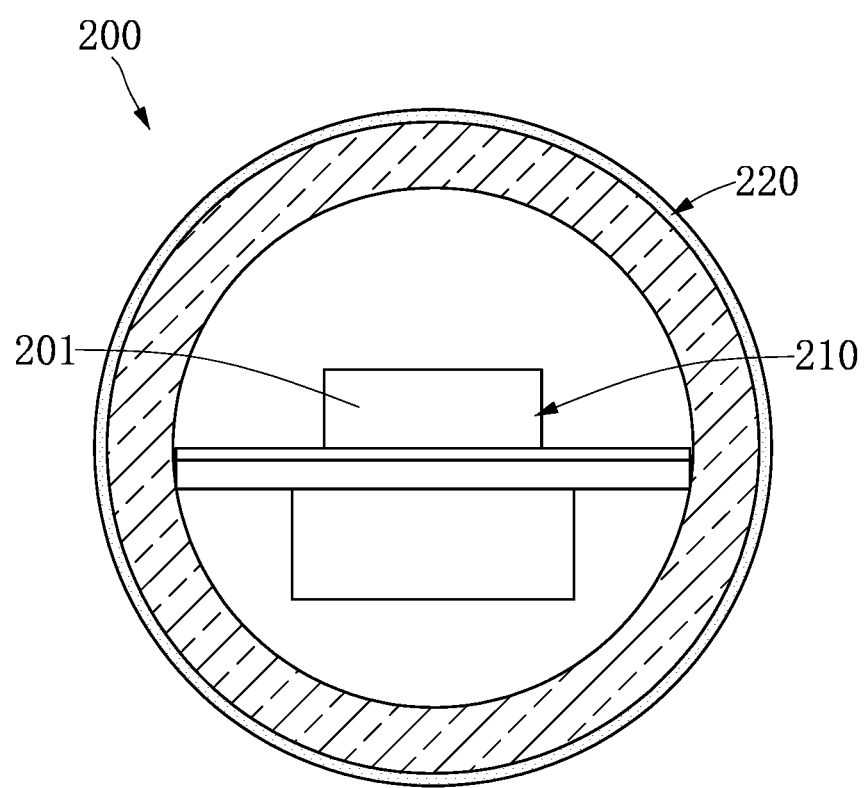
FIG. 3 is another schematic view of the antibacterial lamp applying the circuit configuration method according to the first embodiment of the present disclosure.

Referring to FIG. 1, a first embodiment of the present disclosure provides a circuit configuration method for improving the efficacy of an antibacterial lamp. The circuit configuration method provided in the present embodiment is applied to an antibacterial lamp 200 (as shown in FIG. 2 and FIG. 3). The antibacterial lamp 200 referred to in the present disclosure is a lamp that excites a nanometer coating (e.g., silver ions) to achieve antibacterial effect through a high-voltage electric field generated by light emitting diode chips. According to a current experimental data of the antibacterial lamp 200, when a voltage provided by the light emitting diodes of the antibacterial lamp 200 is increased, the effect of the light emitting diodes of the antibacterial lamp 200 exciting the nanometer coating for antibacterial effect is better. The circuit configuration method includes steps S101 to S107. It should be noted that, any one of the above steps can be omitted or appropriately replaced according to practical requirements.

The step S101 is implemented by providing an alternating voltage to a rectifier circuit and a boost loop.

The step S103 is implemented by using the rectifier circuit to rectify the alternating voltage into a direct voltage and providing a first voltage level.

The step S105 is implemented by using the boost loop to increase the direct voltage to a second voltage level.

The step S107 is implemented by combining the first voltage level and the second voltage level into a high voltage level to provide for a driving circuit to drive the antibacterial lamp.

Accordingly, as shown in FIG. 2 and FIG. 3, a series light emitting diodes 210 (i.e., a plurality of light emitting diodes 201 connected in series) of the antibacterial lamp 200 can generate a high-voltage electric field by a small amount of the light emitting diodes 201, so as to excite a nanometer coating 220 of the antibacterial lamp 200 through a high-voltage electric field to generate antibacterial ions (e.g., silver ions).

In other words, comparing two antibacterial lamps that can provide the same high-voltage electric field, an antibacterial lamp adopting the circuit configuration method provided by the present disclosure can achieve the high-voltage electric field with fewer light emitting diodes, that is, an efficacy of the antibacterial lamp using the circuit configuration method is boosted.

Figure 6:
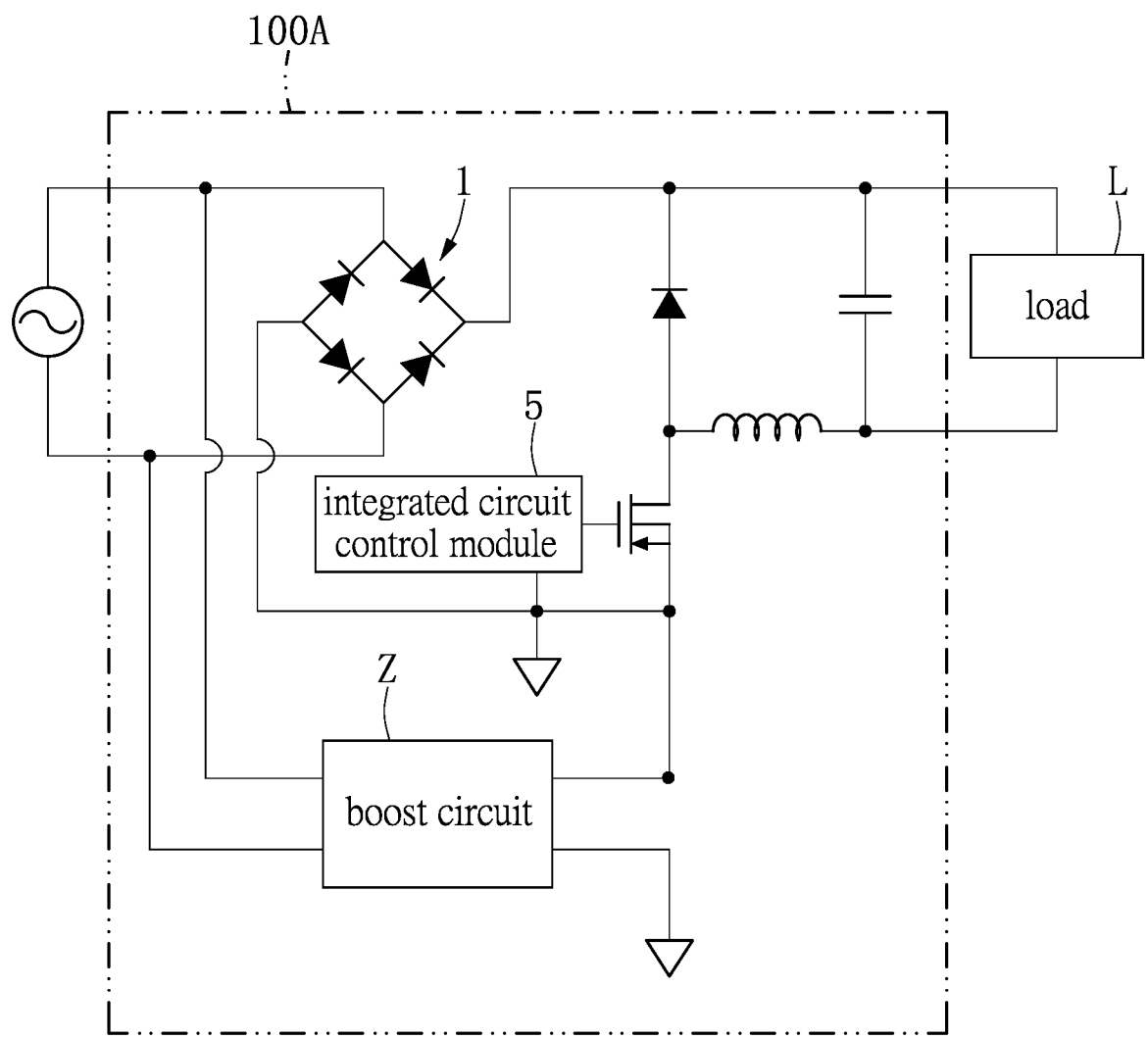
FIG. 6 is a schematic circuit view of another configuration of the voltage boost circuit according to the third embodiment of the present disclosure.
Figure 8:
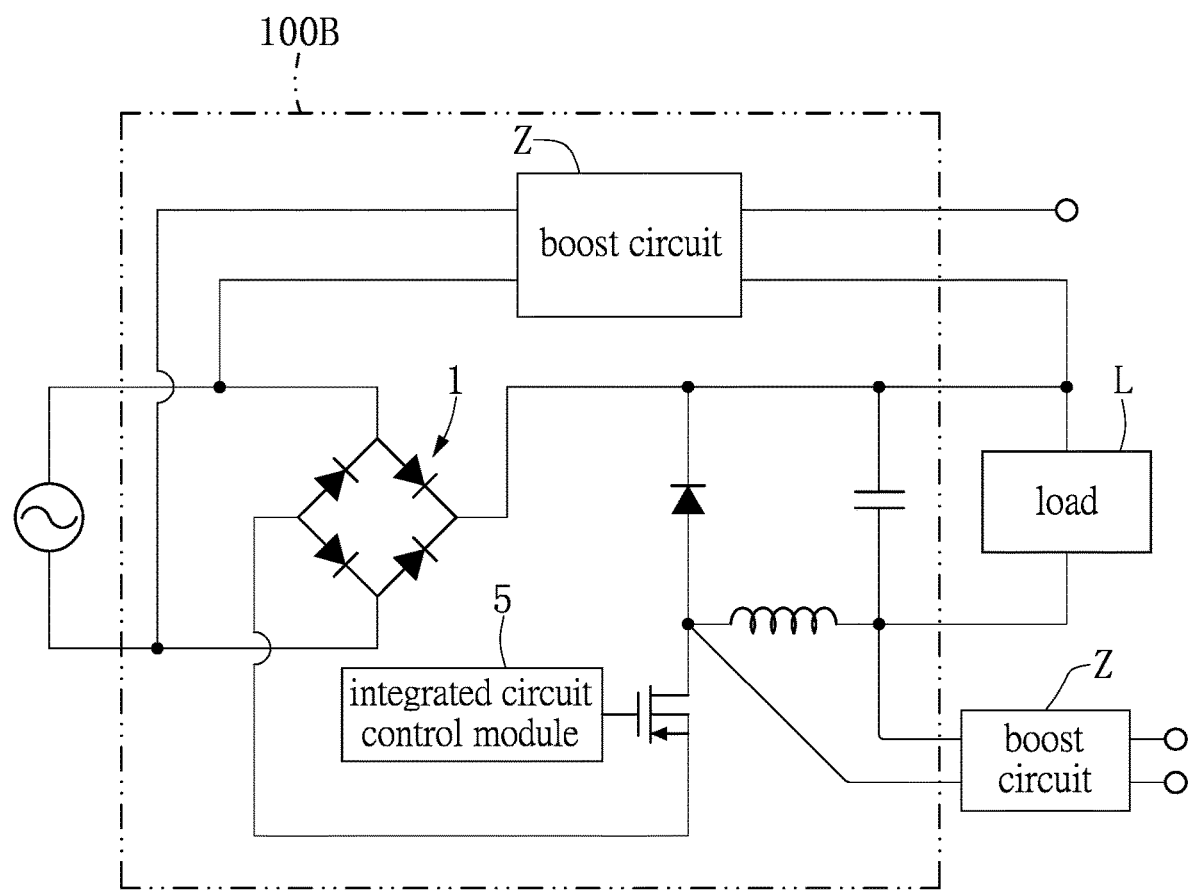
FIG. 8 is a schematic circuit view of yet another configuration of the voltage boost circuit according to the third embodiment of the present disclosure.

Preferably, the circuit configuration method for improving the efficacy of the antibacterial lamp can also include a step that is implemented by combining the first voltage level and the second voltage level into the high voltage level by an integrated circuit control module 5 (e.g., as shown in FIG. 6 and FIG. 8). Accordingly, the user can control a combination relationship between the first voltage level and the second voltage level through the integrated circuit control module 5, so as to control the high voltage level to be generated (i.e., controlling the antibacterial lamp 200 to excite the nanometer coating 220).

In addition, although the circuit configuration method is to convert alternating current to direct current, the circuit configuration method can also be directly supplied by direct current in subsequent steps. That is to say, those skilled in the art can change direct input direct current according to practical requirements.

Second Embodiment

Figure 4:
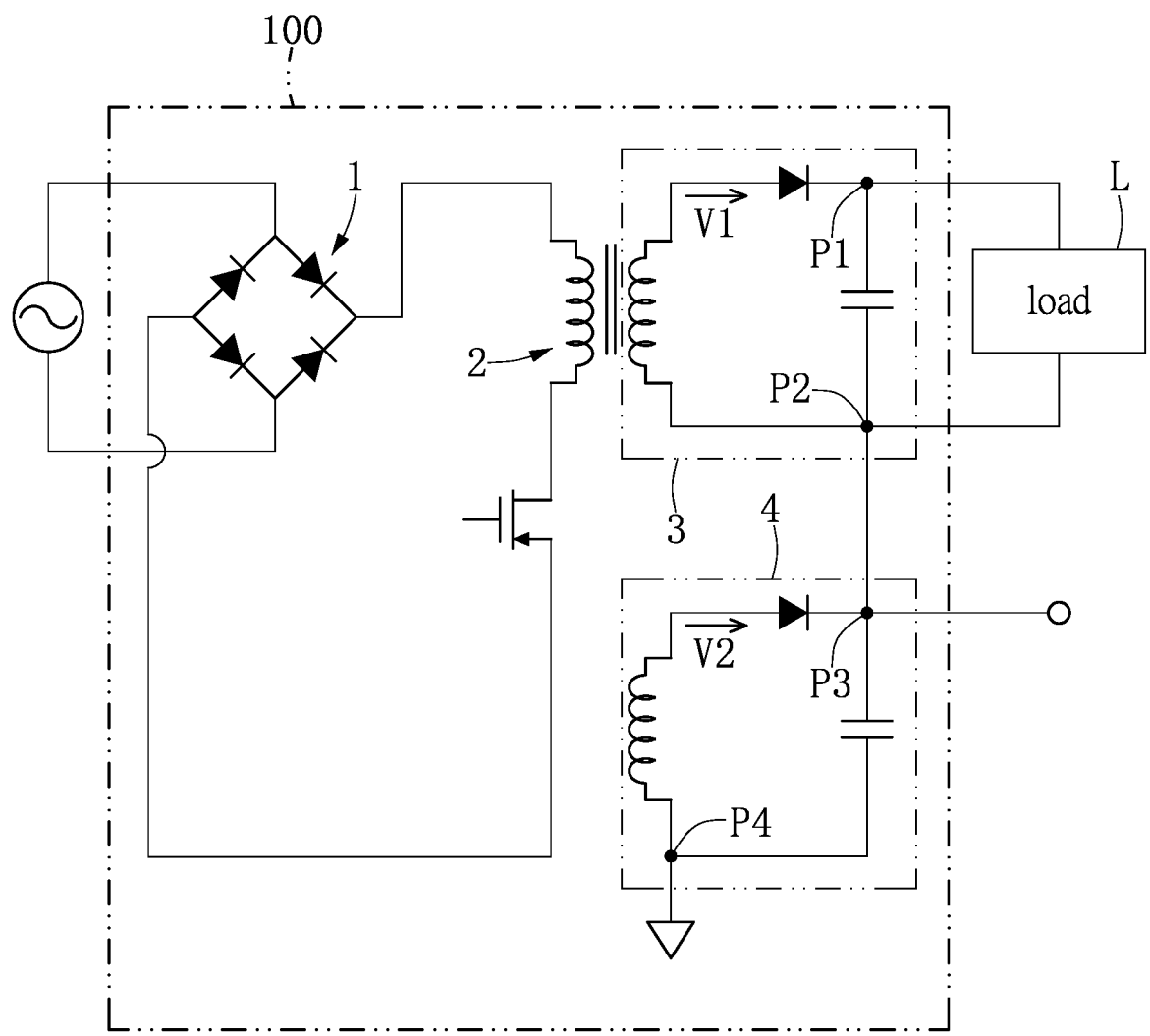
FIG. 4 is a schematic circuit view of a voltage boost circuit according to a second embodiment of the present disclosure.

Referring to FIG. 4, a second embodiment of the present disclosure provides a voltage boost circuit 100 adopting the circuit configuration method in the first embodiment for improving the efficacy of the antibacterial lamp. The voltage boost circuit 100 includes a rectifier module 1, a primary side 2 and a first secondary side 3 electrically coupled to the rectifier module 1, and a second secondary side 4 that is electrically coupled to the first secondary side 3.

The rectifier module 1 in the present embodiment is a full-wave rectifier, and the rectifier module 1 can be used to electrically couple an AC power supply to rectify it into a DC power supply, but the present disclosure is not limited thereto. For example, the rectifier module 1 of the voltage boost circuit 100 can also be replaced by a half-wave rectifier or a voltage doubler rectifier, so as to be used to electrically couple to the AC power supply.

The primary side 2 in the present embodiment is a single one-piece structure, and the primary side 2 can obtain the DC power supply through the rectifier module 1. In other words, the primary side 2 in the present embodiment can be a single winding (or coil) with an iron core as a magnetic circuit. Naturally, in another embodiment of the present disclosure (not shown), a power source obtained by the primary side 2 can be the AC power source, which means that the rectifier module 1 of the voltage boost circuit 100 can be omitted according to practical requirements.

The first secondary side 3 in the present embodiment is disposed on one side of the primary side 2, and an electromagnetic induction occurs between the first secondary side 3 and the primary side 2 to generate a first high voltage V1. In other words, a winding of the first secondary side 3 is adjacent to a winding of the primary side 2, and the winding of the first secondary side 3 does not contact to the winding of the primary side 2. In practical applications, a circuit of the first secondary side 3 has components such as diodes and capacitors (i.e., a rectifier circuit), and can generate the electromagnetic induction with the primary side 2.

In more detail, the first secondary side 3 includes a first connecting terminal and a first ground terminal that is configured to be used to connect one of two connecting ends (e.g., a positive end) of a load L (i.e., the series light emitting diodes 210 of the antibacterial lamp 200), and the first ground terminal is electrically coupled to the second secondary side 4. That is to say, a connection position between the first connecting terminal and the load L has a node P1, and a connection position between the first ground terminal and the second secondary side 4 has a node P2.

The second secondary side 4 in the present embodiment is disposed on one side of the primary side 2, and an electromagnetic induction occurs between the second secondary side 4 and the primary side 2 to generate a second high voltage V2. In other words, a winding of the second secondary side 4 is adjacent to the winding of the primary side 2, and the winding of the second secondary side 4 does not come in contact with the winding of the primary side 2. In practical applications, a circuit of the second secondary side 4 has components such as diodes and capacitors (i.e., a LC circuit), and the second secondary side 4 and the first secondary side 3 each generate an electromagnetic induction with the primary side 2 at the same time. A quantity of turns of the second secondary side 4 is not equal to a quantity of turns of the first secondary side 3, so that a value of the second high voltage V2 is not equal to a value of the first high voltage V1.

Further, the second secondary side 4 includes a second connecting terminal and a second ground terminal that is configured to be used to connect another of the two connecting ends (e.g., a negative end) of the load L, and the second ground terminal is a reference point of a ground potential of the system. That is to say, a connection position between the second connection terminal and the load L has a node P3, and a position of the reference point between the second ground terminal and the ground potential of the system has a node P4.

Accordingly, the voltage boost circuit 100 can make an energy obtained by the load L be a high voltage with a small voltage difference. For ease of understanding, an example will be provided in the following description, but the present disclosure is not limited thereto.

When the load L is a light emitting device including a plurality of light emitting diodes connected in series, and has a need to use silver ions to excite a nano silver through a 1200 volts high-voltage electric field for sterilization, a turns ratio of the primary side 2 to the first secondary side 3 will be designed to be boosted to 100 volts (i.e., a voltage of the node P1 is 100 volts), and a turns ratio of the primary side 2 to the second secondary side 4 is designed to be boosted to 1100 volts (i.e., a voltage of the node P3 is 1100 volts). Therefore, a total voltage of the power supply when the first secondary side 3 and the second secondary side 4 are connected in series with each other will be 1200 volts.

When the positive terminal and the negative terminal of the light emitting device are respectively connected to the first secondary side 3 and the second secondary side 4 through the node P1 and the node P3, a reference voltage to a ground potential of the light emitting device will be a 1100 volts high potential, and a total voltage of the power source obtained by the light emitting device will be 1200 volts. That is to say, the power supply provided by the voltage boosting circuit 100 to the light emitting device is a high voltage with a voltage difference of 100 volts. Accordingly, the voltage obtained by the light emitting diodes of the light emitting device from the positive terminal to the negative terminal will be within a range from 1100 volts to 1200 volts, so as to achieve the effect of high-voltage electric field.

Third Embodiment

Figure 5:
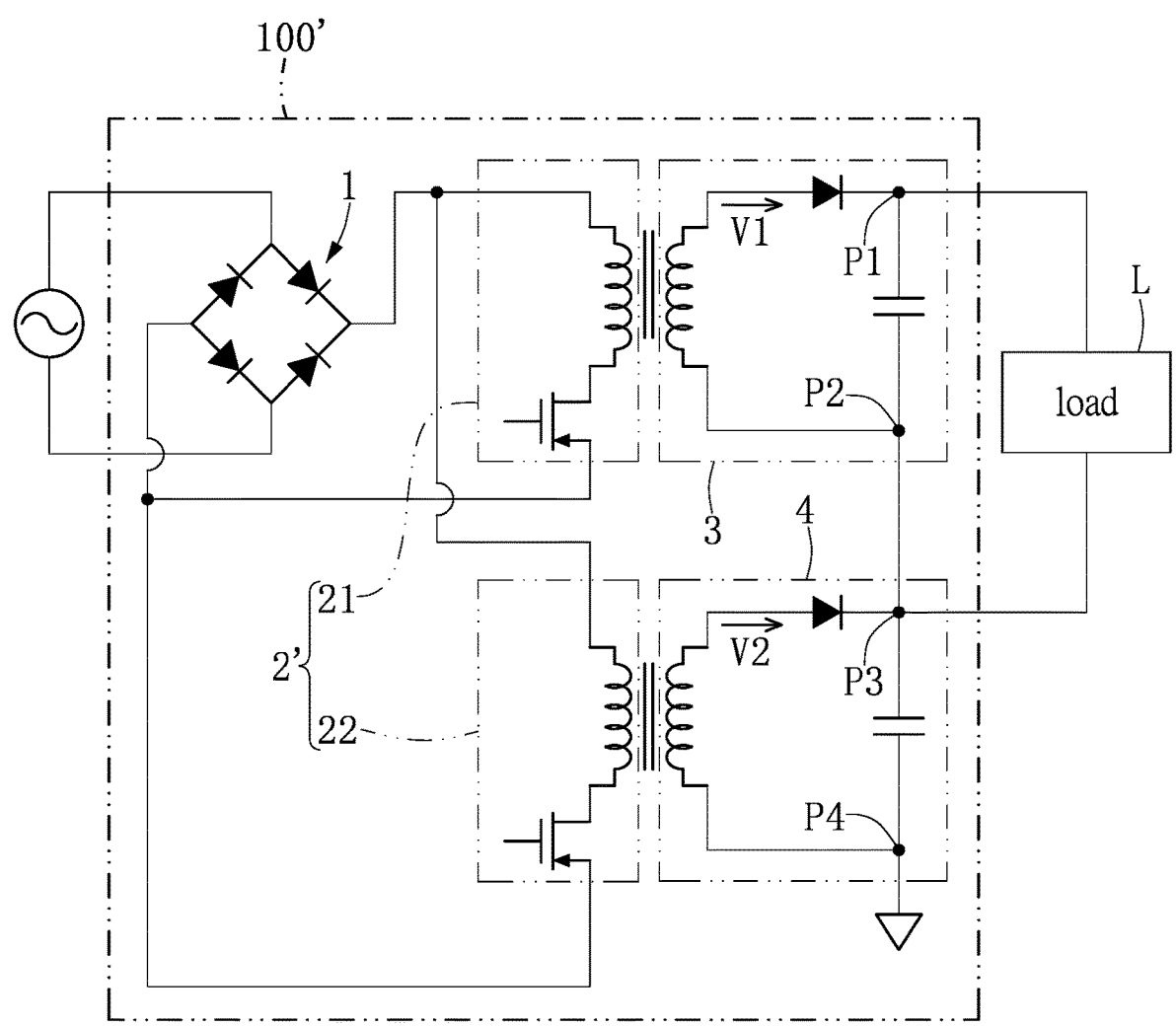
FIG. 5 is a schematic circuit view of the voltage boost circuit according to a third embodiment of the present disclosure.

Referring to FIG. 5, a third embodiment of the present disclosure provides a voltage boost circuit 100', the present embodiment is similar to the voltage boost circuit 100 of the first embodiment, and the similarities therebetween will not be repeated herein. The difference between the present embodiment and the first embodiment mainly resides in that the primary side 2 in the present embodiment is not a single one-piece structure.

Specifically, the primary side 2' in the present embodiment includes a first sub-primary side 21 and a second sub-primary side 22 that are electrically coupled to the rectifier module 1, that is, the primary side 2' has two windings.

In practical applications, the first sub-primary side 21 is disposed on one side of the first secondary side 3, and an electromagnetic induction is generated between the first sub-primary side 21 and the first secondary side 3. The second sub-primary side 22 is disposed on one side of the second secondary side 4, and an electromagnetic induction is generated between the second sub-primary side 22 and the second secondary side 4. In other words, a winding of the first sub-primary side 21 is adjacent to a winding of the first secondary side 3, and the winding of the first sub-primary side 21 does not contact to the winding of the first secondary side 3. A winding of the second sub-primary side 22 is adjacent to a winding of the second secondary side 4, the winding of the second sub-primary side 22 does not contact to the winding of the second secondary side 4.

In practice, a number of turns of the first sub-primary side 21 matches a number of turns of the first secondary side 3, and a number of turns of the second sub-primary side 22 matches a number of turns of the second secondary side 4. Therefore, the number of turns of the first sub-primary side 21 and the number of turns of the second sub-primary side 22 can be designed to be the same or different according to practical requirements.

Based on the first embodiment to the third embodiment, in practical application, the antibacterial lamp 200 may adopt one of voltage boosting circuits 100A, 100B, 100C, and 100D shown in FIG. 6, FIG. 8, FIG. 10, and FIG. 11, and the voltage boost circuits 100A, 100B, 100C, and 100D can combine the first voltage level and the second voltage level into the high voltage level by an integrated circuit control module 5, so as to achieve the effects of the second embodiment and the third embodiment. A boost circuit Z shown in FIG. 6, FIG. 8, FIG. 10, or FIG. 11 is a circuit for boosting the voltage, and the circuit can be realized by including the primary side, the first secondary side, and the second secondary side of the second embodiment or the third embodiment, but the present disclosure is not limited thereto.

Taking the voltage boost circuit 100B of FIG. 8 as an example, the rectifier module 1 can be used to electrically couple an AC power source to output a DC power source. One of two boost circuits Z can boost the AC power supply to provide the first voltage level, and another of the two boost circuits Z can boost the DC power supply to provide the second voltage level. The integrated circuit control module 5 controls the second voltage level to combine with the first voltage level to form a high voltage level, such as to drive an antibacterial lamp.

Figure 11:
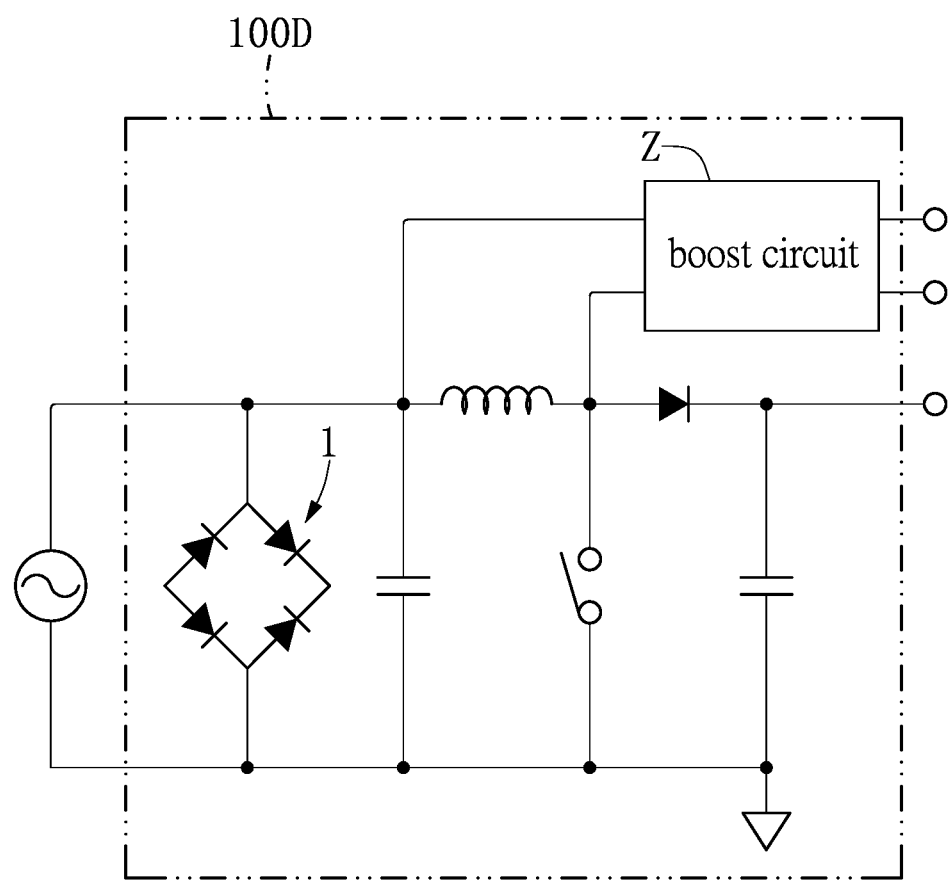
FIG. 11 is a schematic circuit view of still yet another configuration of the voltage boost circuit according to the third embodiment of the present disclosure.

Taking the voltage boost circuit 100D of FIG. 11 as an example, the rectifier module 1 can be electrically coupled to an AC power source to output a DC power source, and the DC power source can provide a first voltage level. The boost circuit Z can provide a second voltage level to the DC power supply, so that the second voltage level can be combined with the first voltage level to form a high voltage level to drive an antibacterial lamp.

Figure 7:
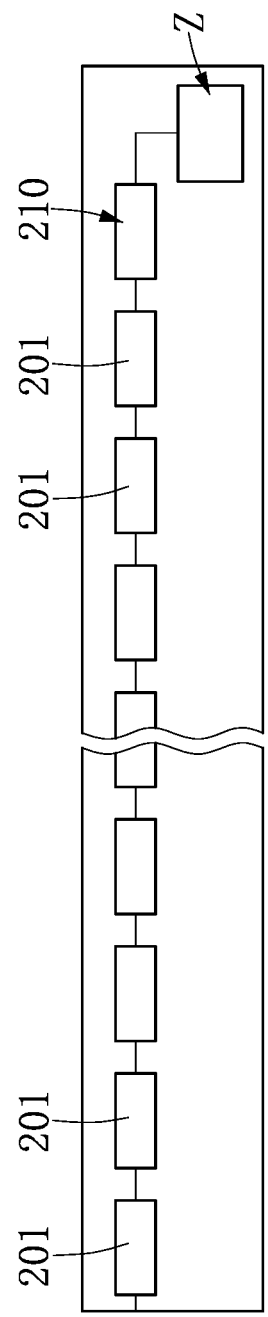
FIG. 7 is a schematic view of the antibacterial lamp applying the another configuration of FIG. 6.
Figure 9:
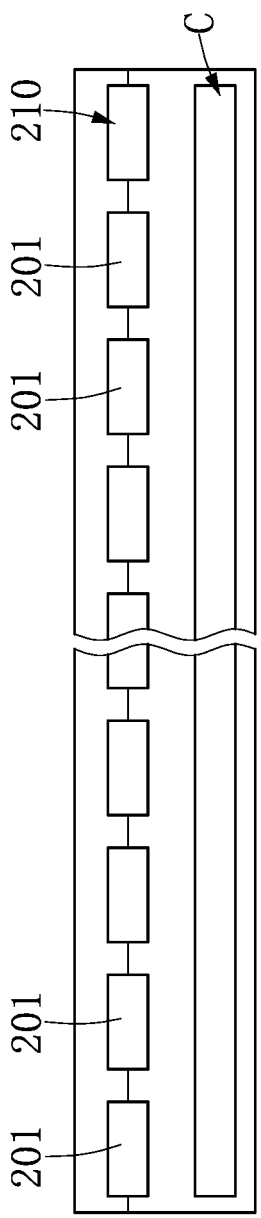
FIG. 9 is a schematic view of the antibacterial lamp applying the yet another configuration of FIG. 8.
Figure 10:
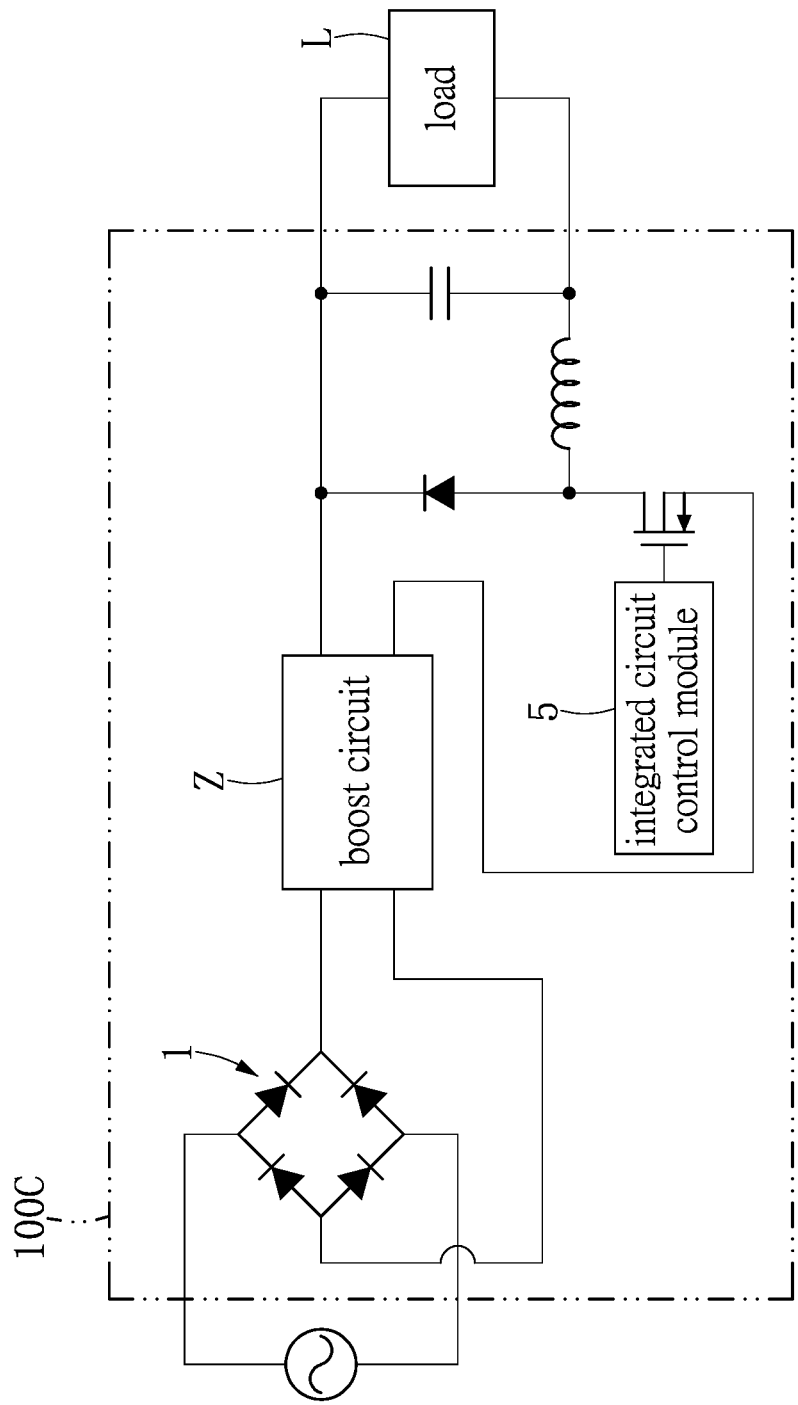
FIG. 10 is a schematic circuit view of still another configuration of the voltage boost circuit according to the third embodiment of the present disclosure.

Moreover, FIG. 7 is a schematic view of a substrate and a string light emitting diode of the antibacterial lamp 100A applying the circuit configuration method, and FIG. 9 is a schematic view of a substrate and a string light emitting diode of the antibacterial lamp 100B applying the circuit configuration method. It can be seen from FIG. 7 and FIG. 9 that the string light emitting diode 210 shown in FIG. 7 can be directly boosted to provide functions such as high-voltage electric field and illumination. The string light emitting diode 210 shown in FIG. 9 can only provide illumination, the high-voltage electric field is provided by a component C (or a circuit) boosted by the boost circuit Z next to the string light emitting diode 210.

Fourth Embodiment

Figure 12:
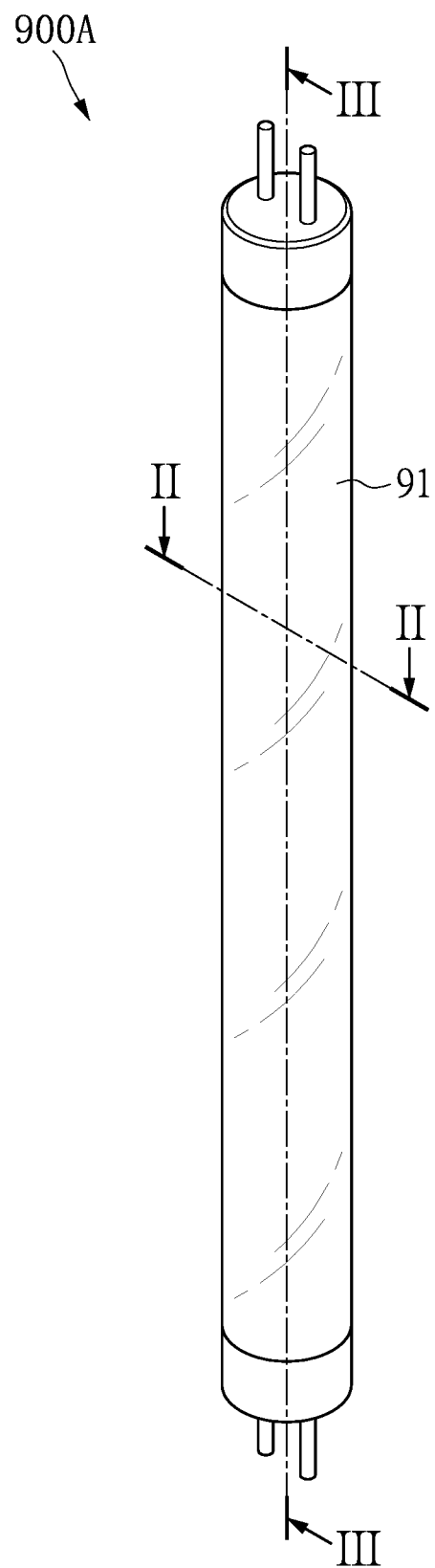
FIG. 12 is a schematic perspective view of an antibacterial lamp according to a fourth embodiment of the present disclosure.
Figure 13:
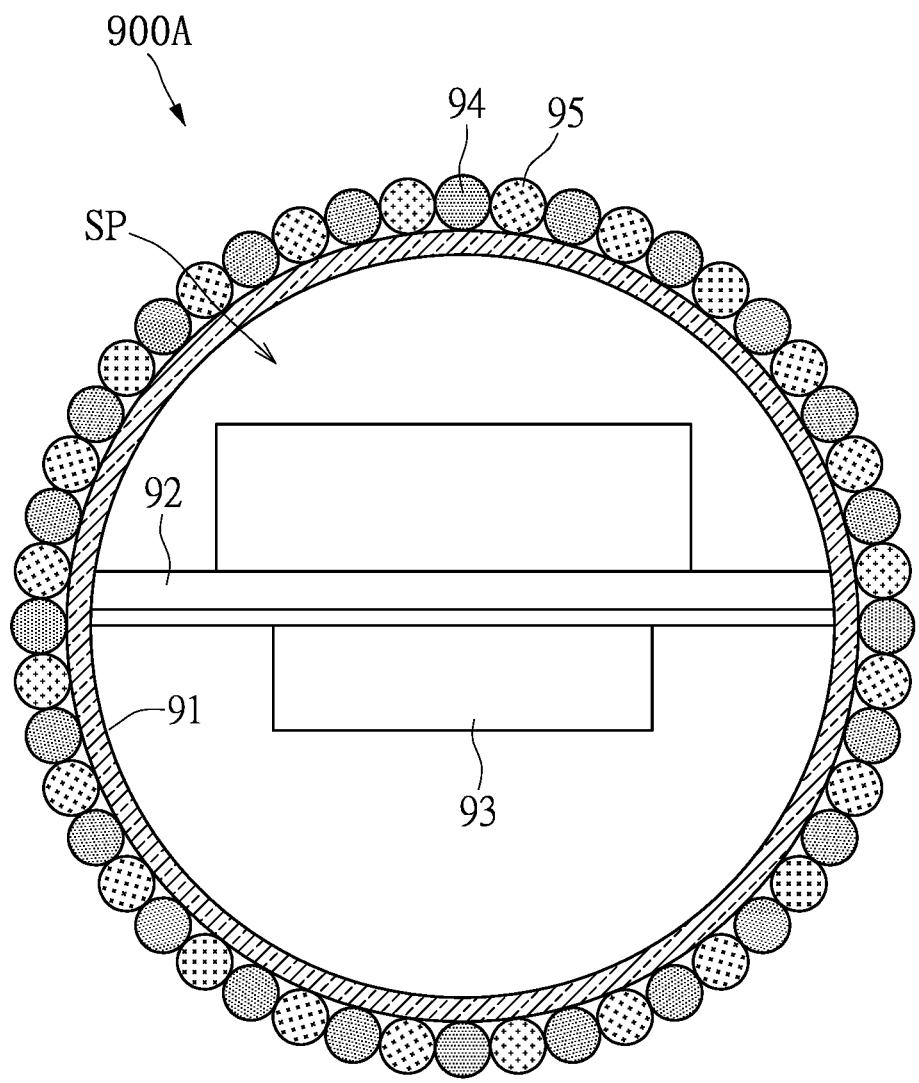
FIG. 13 is a schematic cross-sectional view taken along line II-II of FIG. 12.

Referring to FIG. 12 to FIG. 16, a fourth embodiment of the present disclosure provides an antibacterial lamp 900A. The antibacterial lamp 900A is driven by the circuit configuration method as in the first embodiment (e.g., the antibacterial lamp 900A includes a voltage boost circuit as in the second embodiment or the third embodiment for driving). As shown in FIG. 12 and FIG. 13, the antibacterial lamp 900A includes a translucent cover 91, a substrate 92 disposed in the translucent cover 91, a plurality of light emitting diode chips 93 disposed on the substrate, and a nanometer coating 94 and a photocatalyst coating 95 (e.g., TiO2) that are arranged on the translucent cover 91.

Figure 16:
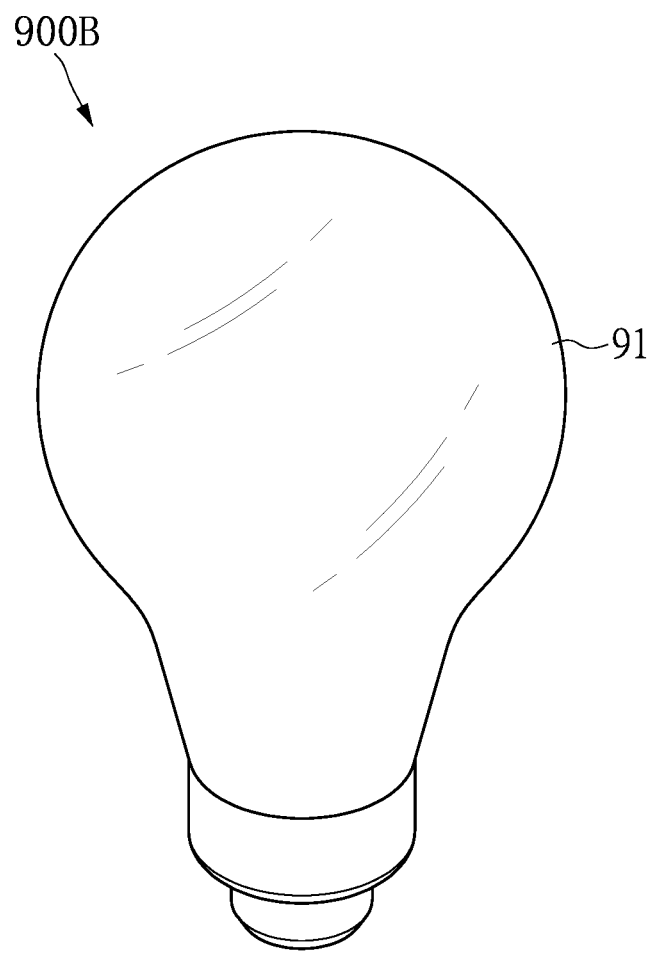
FIG. 16 is another schematic perspective view of the antibacterial lamp according to the fourth embodiment of the present disclosure.
Figure 17:
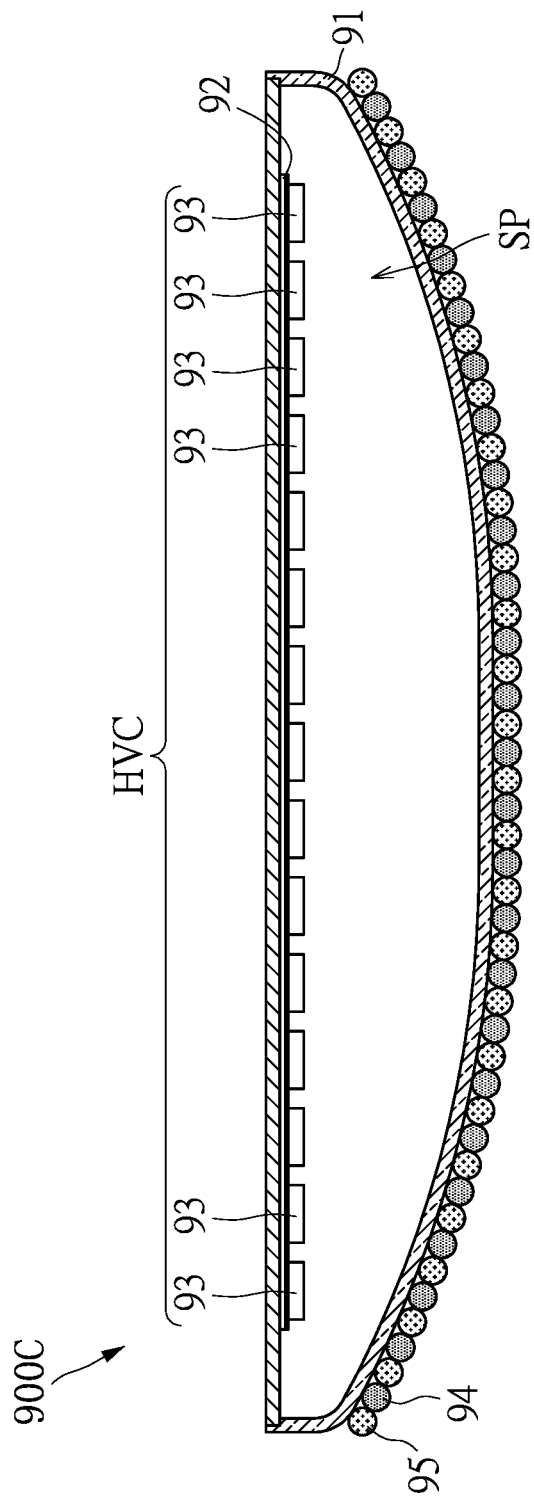
FIG. 17 is yet another schematic perspective view of the antibacterial lamp according to the fourth embodiment of the present disclosure.

Referring to FIG. 12 and FIG. 13, the translucent cover 91 in the present embodiment is a tubular hollow structure made of light-transmitting materials (e.g., a glass, or a transparent acrylic, etc.), and the translucent cover 91 has an accommodating space SP, but a shape of the translucent cover 91 can be adjusted according to practical requirements. For example, in another aspect as shown in FIG. 16, the translucent cover 91 of the antibacterial lamp 900B can also be designed in the shape of a common light bulb. In yet another aspect as shown in FIG. 17, the translucent cover 91 of the antibacterial lamp 900C can also be designed as a flat shape (e.g., a ceiling lamp).

Figure 14:
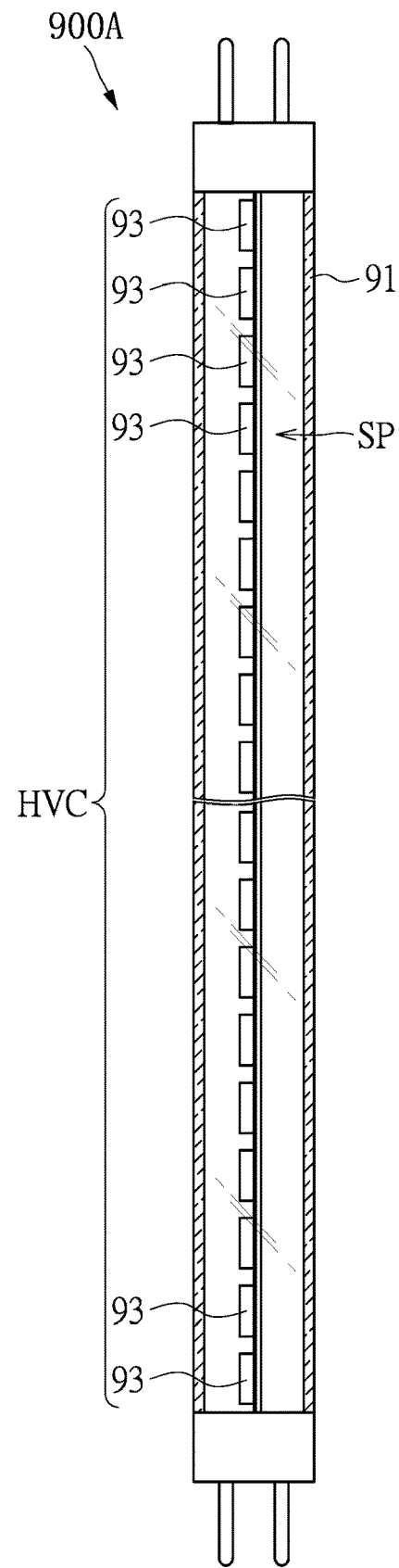
FIG. 14 is a schematic cross-sectional view taken along line III-III of FIG. 12.
Figure 18:
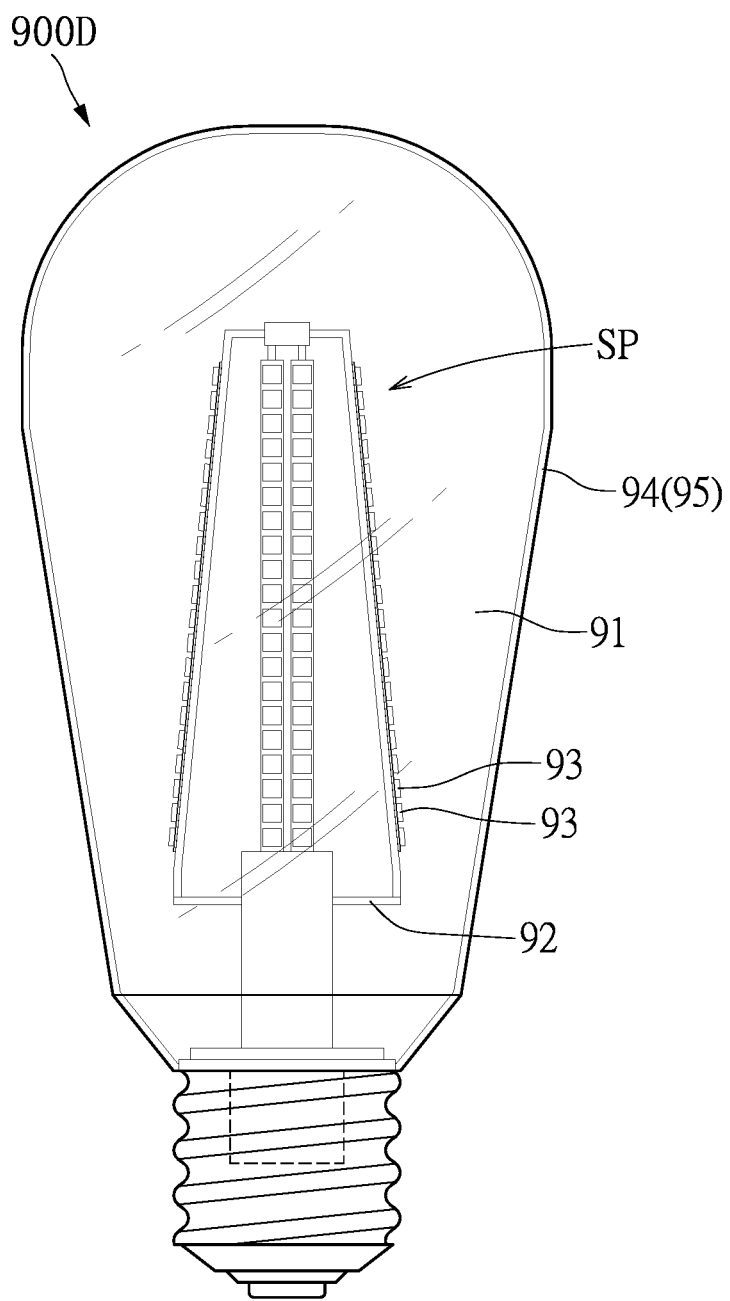
FIG. 18 is still another schematic perspective view of the antibacterial lamp according to the fourth embodiment of the present disclosure.

Referring to FIG. 13 and FIG. 14, the substrate 92 is disposed in the accommodating space SP, and the substrate 92 in the present embodiment is a long plate-shaped structure. The light emitting diode chips 93 are evenly arranged on the substrate 92, and the light emitting diode chips 93 are jointly connected in series to form a high-voltage circuit HVC. When the high-voltage circuit HVC is powered, the high-voltage circuit HVC is configured to generate a high-voltage electric field HE surrounding the translucent cover 91. Naturally, FIG. 13 and FIG. 14 are one of the embodiments of the present disclosure, but the present disclosure is not limited thereto. For example, the application of the present disclosure can also be an antibacterial lamp 900D as shown in FIG. 18, which means that the substrate 92 and the light emitting diode chips 93 are disposed in an arrangement that mimics that of a filament bulb.

It should be noted that the "high-voltage" referred to in the term "high-voltage circuit" refers to a voltage higher than 100 volts of conventional lamps on the market, so that the high-voltage circuit HVC can generate the high-voltage electric field HE with sufficient energy to irradiate the nanometer coating 94. The voltage of the high-voltage circuit HVC is preferably greater than or equal to 400 volts, but the present disclosure is not limited thereto.

Preferably, based on voltage specifications of conventional light emitting diode chips currently on the market, a total quantity of the light emitting diode chips 93 is preferably greater than or equal to 80, so that the high-voltage circuit HVC formed by connecting the light emitting diode chips 93 in series can have the aforementioned high voltage. Moreover, under a configuration where the total quantity of the light emitting diode chips 93 is greater than or equal to 80, a light pattern (or an illuminated area) jointly formed by light emitted from the light emitting diode chips 93 can be more uniform, and the light emitting diode chips 93 can have a better heat uniformity.

Figure 15:
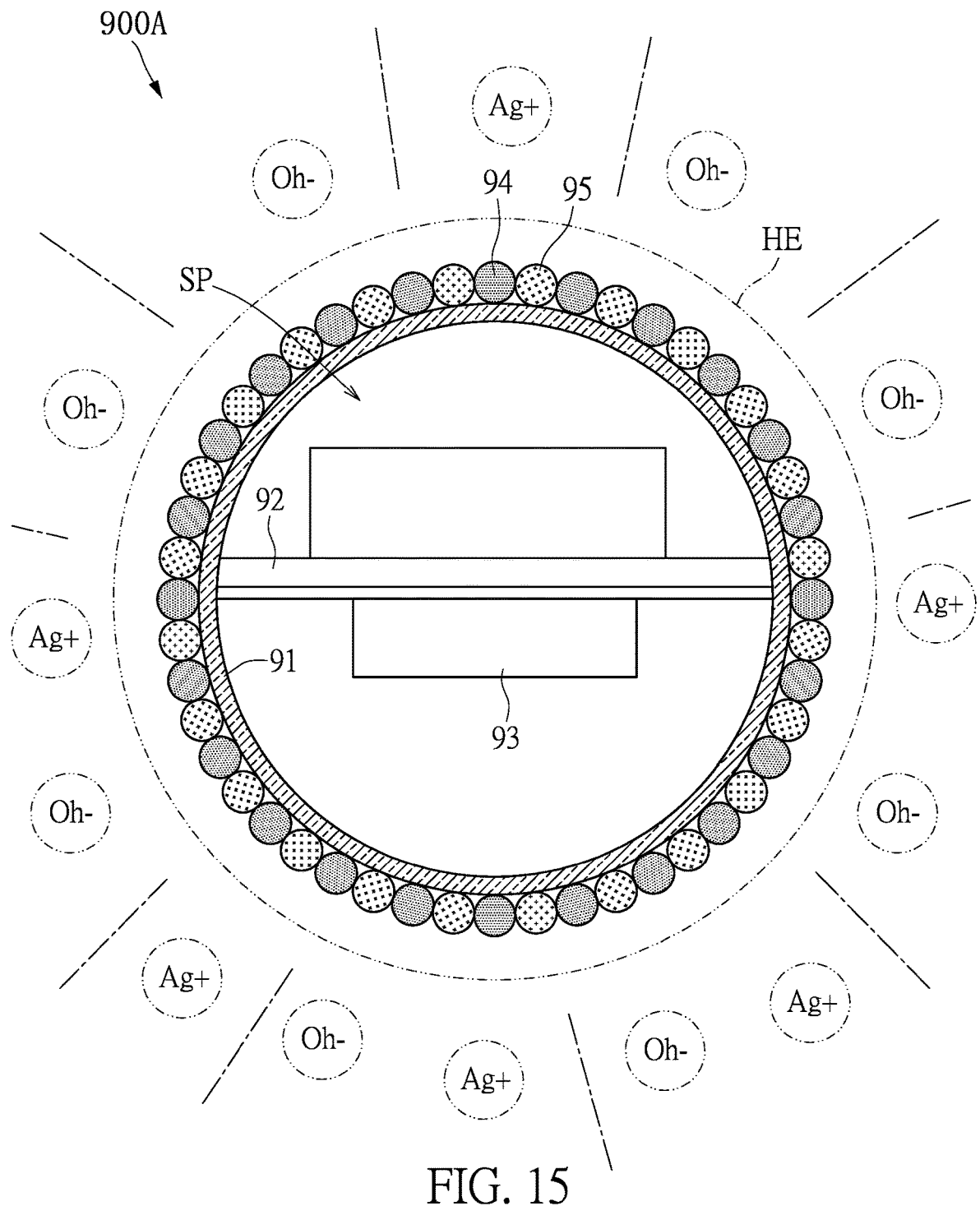
FIG. 15 is a schematic state view showing the antibacterial lamp generate nano silver ions and hydroxide ions according to the fourth embodiment of the present disclosure.

Referring to FIG. 13 and FIG. 15, the nanometer coating 94 and the photocatalyst coating 95 in the present embodiment are uniformly coated on or mixed in an outer side of the translucent cover 91, and a thickness of each of the nanometer coating 94 and the photocatalyst coating 95 is designed to not affect the light produced by the light emitting diode chips 93 from passing, but the present disclosure is not limited thereto. For example, the nanometer coating 94 and the photocatalyst coating 95 can also be coated or mixed on an inner side of the translucent cover 91.

When the nanometer coating 94 is irradiated by the high-voltage electric field HE or irradiated by the light generated by the light emitting diode chips 93, the nanometer coating 94 can further dissociate antibacterial ions. In practice, the nanometer coating 94 can be nano silver, nano-copper or nano-zinc, that is, the antibacterial ions can be nano silver ions, nano-copper ions, or nano-zinc ions, but the present disclosure is not limited thereto. The antibacterial ions in the present embodiment are represented by nano silver ions.

The photocatalyst coating 95 can be irradiated by the light emitting diode chips 93 to dissociate hydroxide ions (OH—). Accordingly, the antibacterial ions and the hydroxide ions that are dissociated can be distributed to the surrounding environment of the translucent cover 91 to inhibit the growth or reproduction of microorganisms.

It should be emphasized that when the quantity of the light emitting diode chips 93 is greater than or equal to 80, a thermal energy generated by the light emitting diode chips 93 can be evenly conducted to the photocatalyst coating 95, so that the photocatalyst coating 95 can be heated by the light emitting diode chips 93 to increase the activity, thereby facilitating the efficiency of the photocatalyst coating 95 being irradiated by the light to generate hydroxide ions.

In addition, it is worth noting that light generated the light emitting diode chips 93 in the present embodiment can be used as illumination light (e.g., white light), and cooperate with the high voltage electric field generated by a large quantity of the light emitting diode chips 93 connected in series to generate antibacterial ions and hydroxide ions. Accordingly, without affecting human health, the antibacterial lamp 900A of the present disclosure can provide good lighting and antibacterial effects at the same time.

In other words, any antibacterial lamp that does not have "the high voltage electric field generated by a large quantity of the light emitting diode chips 93 connected in series to generate antibacterial ions" is not the antibacterial lamp of the present disclosure, nor is "the light emitting diode chips that generate light that is harmful to human health (e.g., ultraviolet light)." For example, an antibacterial lamp that generates a low voltage electric field by connecting a small quantity of the light emitting diode chips (e.g., 10) in series with a boost converter or an antibacterial lamp that combines photocatalysts and antibacterial ions with ultraviolet rays, because the antibacterial lamps of the aforementioned example fails to reach the technical effect of the present disclosure.

Naturally, in another embodiment of the present disclosure (not shown), the antibacterial lamp can also only be coated or mixed with the nanometer coating 94 according to practical requirements, so that antibacterial ions can be dissociated from the antibacterial lamp through the nanometer coating to inhibit the growth or reproduction of microorganisms, which also has the technical effect of the present disclosure.

It is worth mentioning that, when the light emitting diode chips 93 are connected in series and arranged in a straight line, the voltage of the high-voltage electric field will decrease with a connection sequence. For example, when the voltage corresponding to a first one of the light emitting diode chips 93 is 1200 volts, the voltage corresponding to middle one (i.e., the N/2th) of the light emitting diode chips 93 will be 600 volts, and the voltage corresponding to last one (i.e., the Nth) of the light emitting diode chips 93 will be 3 volts. In other words, in the light emitting diode chips 93 arranged in a straight line, half of the light emitting diode chips 93 may not have a voltage field sufficient to generate antibacterial ions and hydroxide ions.

As shown in Table 1 below, Table 1 is data obtained by using the ATP bioluminescence method. It can be clearly seen from Table 1 that when a voltage of the light emitting diode chips 93 is 100 volts (V), an antibacterial effect (i.e., a bacterial reduction) that can be achieved when the nanometer coating 94 is irradiated by the light emitting diode chips 93 is about 21.9%. When a voltage of the light emitting diode chips 93 is 1200 volts (V), an antibacterial effect (i.e., a bacterial reduction) that can be achieved when the nanometer coating 94 is irradiated by the light emitting diode chips 93 is about 86.8%. In other words, although the light emitting diode chips 93 connected to the low voltage can cooperate with the nanometer coating 94 to have an antibacterial effect, an antibacterial effect achieved by the light emitting diode chips 93 connected to the high voltage is higher.

TABLE 1

| The voltage to which the light emitting diode chips are connected | The amount of bacteria in the original environment (RLU) | The amount of bacteria in the environment after being illuminated (RLU) | Bacteria reduction |
| --- | --- | --- | --- |
| Low voltage (100 V) | 10382 | 8105 | 21.9% |
| High voltage (1200) | 12941 | 1707 | 86.8% |

Figure 19:
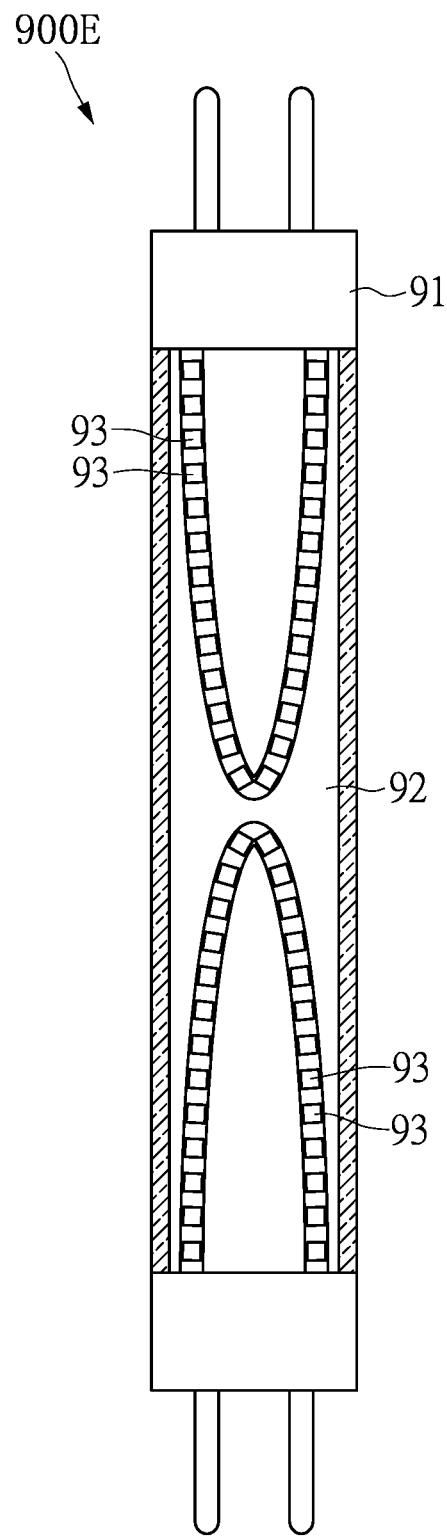
FIG. 19 is still yet another schematic perspective view of the antibacterial lamp according to the fourth embodiment of the present disclosure.
Figure 20:
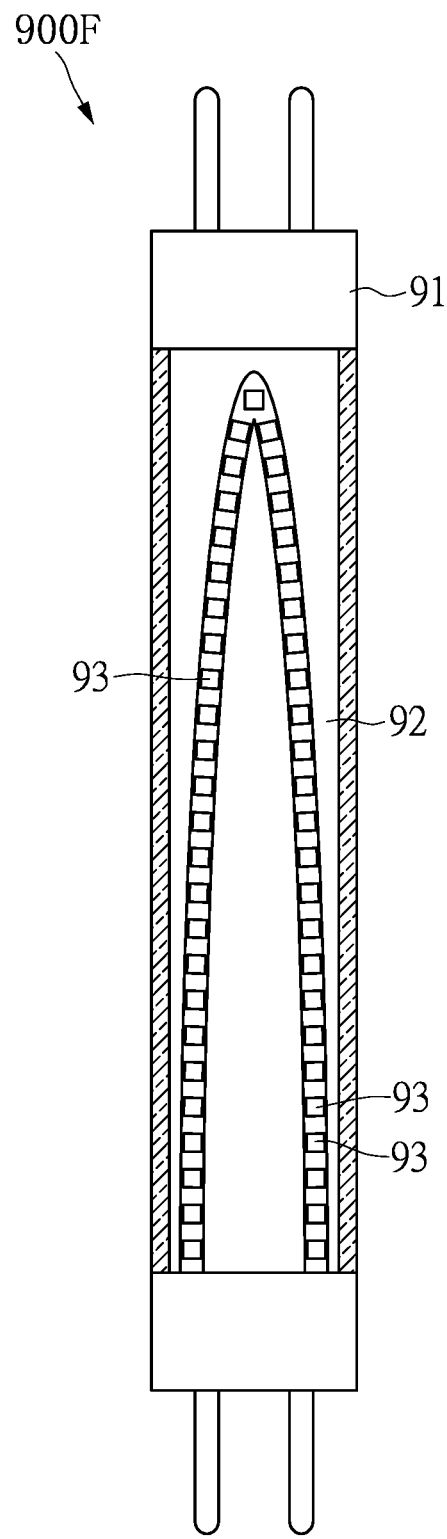
FIG. 20 is still yet another schematic perspective view of the antibacterial lamp according to the fourth embodiment of the present disclosure.

Therefore, as shown in FIG. 19 and FIG. 20, the light emitting diode chips 93 of the antibacterial lamps 900E and 900F in the present disclosure adopt a U-shaped arrangement design, so that the light emitting diode chips 93 are arranged in the translucent cover 91 to form two U-shaped facing each other, or a single U-shape. The antibacterial lamps 900E and 900F can ensure that the nanometer coating 94 and the photocatalyst coating 95 on the translucent cover 91 can be irradiated and covered by the first to N/2th light emitting diode chips with a high-voltage electric field.

Beneficial Effects of the Embodiments

In conclusion, the circuit configuration method, the voltage boost circuit, and the antibacterial lamp provided by the present disclosure, by virtue of "the first voltage level and the second voltage level being combined into a high voltage level," the circuit configuration method, the voltage boost circuit, and the antibacterial lamp can provide a high voltage with a small load voltage difference to improve the antibacterial effect of the antibacterial lamp.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A circuit configuration method for improving the efficacy of an antibacterial lamp, the circuit configuration method comprising:
   providing an alternating voltage to a rectifier circuit and a boost loop;
   using the rectifier circuit to rectify the alternating voltage into a direct voltage and providing a first voltage level;
   using the boost loop to increase the direct voltage to a second voltage level; and
   combining the first voltage level and the second voltage level into a high voltage level to provide for a driving circuit to drive the antibacterial lamp.

2. The circuit configuration method according to claim 1, further comprising:
   combining the first voltage level and the second voltage level into the high voltage level by an integrated circuit control module.

3. An antibacterial lamp derived by the circuit configuration method as claimed in claim 1, the antibacterial lamp comprising:
   a translucent cover having an accommodating space;
   a substrate disposed in the accommodating space;
   a plurality of light emitting diode chips disposed on the substrate, wherein the light emitting diode chips are connected in series to form a high-voltage circuit, wherein, when the high-voltage circuit is powered, the high-voltage circuit is configured to generate a high-voltage electric field surrounding the translucent cover; and
   a nanometer coating disposed on the translucent cover, wherein the nanometer coating is configured to be irradiated by the high-voltage electric field to dissociate antibacterial ions.

4. The antibacterial lamp according to claim 3, further comprising a photocatalyst coating that is configured to be irradiated by the light emitting diode chips to dissociate hydroxide ions.

5. The antibacterial lamp according to claim 4, wherein the nanometer coating and the photocatalyst coating are coated on the translucent cover or mixed in the translucent cover.

6. The antibacterial lamp according to claim 3, wherein a total quantity of the light emitting diode chips is greater than or equal to 80.

7. The antibacterial lamp according to claim 3, wherein a voltage of the high-voltage circuit is greater than or equal to 400 volts.

8. The antibacterial lamp according to claim 3, wherein the light emitting diode chips in the translucent cover are arranged in two U-shapes that are opposite to each other.

9. The antibacterial lamp according to claim 3, wherein the light emitting diode chips in the translucent cover are arranged in a U-shape.

10. A voltage boost circuit for an antibacterial lamp, comprising:
    a primary side;
    a first secondary side including a first connecting terminal and a first grounding terminal, wherein a first high voltage is generated between the first secondary side and the primary side by electromagnetic induction; and
    a second secondary side electrically coupled to the first ground terminal, wherein a second high voltage is generated between the second secondary side and the primary side by electromagnetic induction that is not equal to the first high voltage, and wherein the second secondary side includes a second connecting terminal, and the second connecting terminal and the first connecting terminal are configured to be used to connect with a load.

11. The voltage boost circuit according to claim 10, further comprising a rectifier module electrically coupled to the primary side, wherein the rectifier module is configured to electrically couple an AC power source to output a DC power source to the primary side.

12. The voltage boost circuit according to claim 11, wherein the primary side includes a first sub-primary side and a second sub-primary side that are electrically coupled to the rectifier module, wherein the first sub-primary side is disposed on one side of the first secondary side, and an electromagnetic induction is generated between the first sub-primary side and the first secondary side, and wherein the second sub-primary side is disposed on one side of the second secondary side, and an electromagnetic induction is generated between the second sub-primary side and the second secondary side.

13. The voltage boost circuit according to claim 12, wherein the primary side is a single one-piece structure, the first secondary side and the second secondary side are disposed on one side of the primary side, and an electromagnetic induction is generated between the first secondary side and the second secondary side at the same time.

14. A voltage boost circuit for providing an antibacterial lamp, comprising:
    a rectifier module configured to electrically couple an AC power source to output a DC power source;
    two boost loops, wherein one of the two boost loops is configured to boost the AC power source to provide a first voltage level, and another one of the two boost loops is configured to boost the DC power source to provide a second voltage level; and
    an integrated circuit control module controlling the second voltage level to be combined with the first voltage level to form a high voltage level, so as to drive the antibacterial lamp.

* * * * *